United States Patent [19]

Krbechek et al.

[11] 4,252,732

[45] Feb. 24, 1981

[54] PROCESSING OF STEROIDS CONTAINING AMINO FUNCTIONALITY

[75] Inventors: Leroy O. Krbechek; Ernest B. Spitzner, both of Minneapolis; James P. Clark, Forest Lake, all of Minn.

[73] Assignee: Henkel Corporation, Minneapolis, Minn.

[21] Appl. No.: 122,396

[22] Filed: Feb. 19, 1980

[51] Int. Cl.$^3$ .............................................. C07J 9/00
[52] U.S. Cl. .............................. 260/397.3; 260/397.1
[58] Field of Search ..................................... 260/397.3; /Machine Searched Steroids

[56] References Cited

U.S. PATENT DOCUMENTS

| | | | |
|---|---|---|---|
| 3,149,102 | 9/1964 | Georgian et al. | 260/239.5 |
| 3,591,611 | 7/1971 | Arth et al. | 260/397.3 |

*Primary Examiner*—Elbert L. Roberts
*Attorney, Agent, or Firm*—Forrest L. Collins; Patrick J. Span

[57] ABSTRACT

The present invention describes the conversion of steroids having a 20-amino functionality to progesterone and other useful steroids.

21 Claims, No Drawings

PROCESSING OF STEROIDS CONTAINING AMINO FUNCTIONALITY

BACKGROUND OF THE INVENTION

1. Field of the Invention

The present invention relates to obtaining steroid compounds from their amino precursors.

2. Description of the Art

This invention deals basically with the conversion of steroid compounds having an acid side chain to give useful intermediates and end compounds such as progesterone.

For instance, in published European patent application No. 4-913 dated Oct. 31, 1979, it was revealed that through microbiological transformation that it was possible to obtain a substantial yield of steroids having a 20 carbonyl functionality. It has also been observed that through following the teachings of the European patent that it is also possible to obtain 3-oxo-pregna-1,4,17(20)-triene-20-carboxylic acid. Of course, depending upon the pH of the solution, it is possible to obtain the carbonyl compounds as either the acid or salt or mixtures thereof.

Jiu, et al, in U.S. Pat. No. 3,994,933, issued Nov. 30, 1976, describes the process of obtaining 3-oxo-pregna-4,17(20)-diene-20-carboxylic acid and its esters through microbiological degradation of several basic sterols. Previously, Julian in JACS Vol. 70, published Apr. 3, 1948, No. 3, at page 887, describes several steroids having an acid functionality in the side chain. Steroidal acids and their derivatives are discussed in U.S. Pat. No. 4,088,760 issued to Bensen, et al., on May 9, 1978.

Derivatives of steroids are discussed in U.S. Pat. No. 2,566,336 issued to Julian, et al., Sept. 4, 1951, and in British Pat. No. 1,043,018 to Meyer, et al., published Sept. 21, 1966. Ruschig, et al, discusses steroids in U.S. Pat. No. 2,731,461 issued Jan. 17, 1956, and in an article published Feb. 21, 1955, in Chemische Berichte Jahrg.88, Number 6, 1955, pages 883–894. Additional steroid products are discussed in U.S. Pat. No. 2,752,369 issued to Holysz et al, on June 26, 1956 and U.S. Pat. No. 3,519,658 issued July 7, 1970.

Still more steroids are reported in "The Oxidation of Steroidal Amines to Nitro Steroids" by Robinson, et al, Volume 31, J. Am. Chem. Soc. 1956, p. 524 et seq. A second article discussing amine steroids is found at Tetrahedron Letters, No. 18, pp. 1053–1061 (1964) by Tomita, et al. Amines are generally discussed by Corey, et al, J. Am. Chem. Soc., Vol. 91, #6, pp. 1429-32 (1969), and by Dinizo, et al, at J. Am. Chem. Soc., Vol. 97 #23, pp. 6900–6901 (1975).

Additional references which discuss compounds having acid side chains and their conversion into useful steroids include the article of Wieland, et al, published in Helvetica Chimica Acta, Vol. 32, part V (1949) No. 233 at page 1764. In another article in the same journal, steroids having an acid side chain are described by Meystre, et al, at Helvetica Chimica Acta, Vol. 32, part V (1949) No. 232 at page 1758. Similarly, Wieland, et al, at Helvetica Chimica Acta, Vol. 32, Part VI, (1949, No. 255 at page 1922 again describes the transformation of steroids having an acid side chain.

To the extent that each of the foregoing references are applicable to the present invention, they are herein incorporated by reference.

Throughout the present invention, percentages and ratios are given by weight unless otherwise indicated and temperatures are in degrees Celsius unless otherwise indicated.

SUMMARY OF THE INVENTION

The present invention describes a process for the conversion of a member selected from the group consisting of 20-amino-3-oxo-pregn-4-ene, and 20-amino-3-oxo-pregna-1,4-diene and mixtures thereof to 3,20-dioxo-pregn-4-ene and 3,20-dioxo-pregna-1,4-diene and mixtures thereof comprising:

(a) obtaining the 20-amino-3-oxo-pregn-4-ene and 20-amino-3-oxo-pregna-1,4-diene in the form of the free amine;

(b) contacting the free amine of (a) with a 3,5-disubstituted orthoquinone in a sufficient amount to form the corresponding steroidal anil; and, (c) hydrolyzing the steroidal anil formed in (b) to obtain the 3,20-dioxo-pregn-4-ene and 3,20-dioxo-pregna-1,4-diene and mixtures thereof.

DETAILED DESCRIPTION OF THE INVENTION

The present invention requires obtaining a member selected from the group consisting of 20-amino-2-oxo-pregna-1,4-diene and 20-amino-3-oxo-pregn-4-ene and mixtures thereof.

Shown below in A and B are the parent compounds for the described amines. The acids shown at C and D may be reduced in the 17(20) position to A and B.

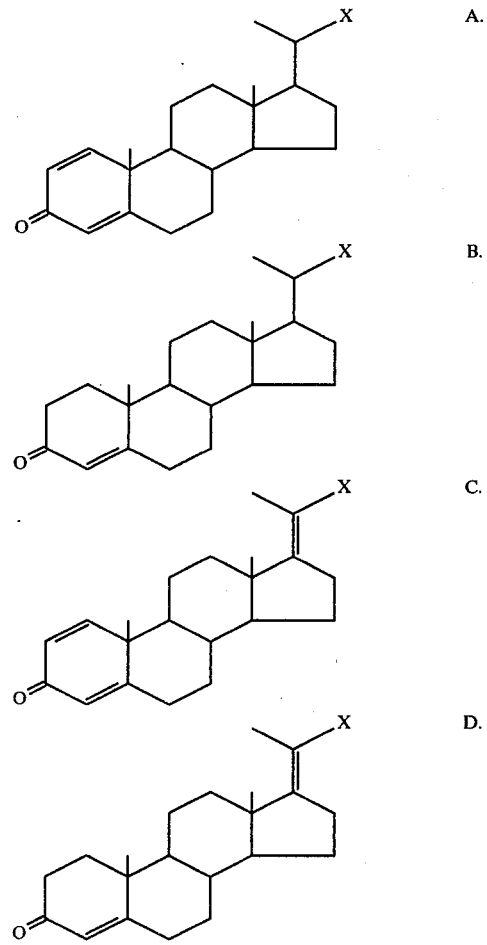

In the formulas above when X is COOH the parent acid is shown. The acid may be converted to the acid chloride (halide) where X is COCl and thereafter to the amide X being CONH$_2$, followed by conversion to the isocyanate X=NCO and thereafter to the carbamate where X=NH(CO$_2$)CH$_3$ via the bromoamide X=CONHBr. Finally, the carbamate is hydrolyzed to the amine where X is NH$_2$.

The free amine may be obtained directly or it may be obtained as a salt such as the hydrochloride, the bisulfate, or other similar salts. When the amine is initially present as a salt, it is necessary to treat the amine salt with a base to obtain the free amine.

In any event, the free amine is then contacted with a 3,5-di substituted orthoquinone in a sufficient amount to form a steroidal anil. It is believed that through a series of reactions the 3,5-di-substituted orthoquinone causes the steroidal amine nitrogen, while still attached to the 20 carbon of the steroid structure, to form a double bond to the quinone ring structure in an ortho position relative to the carbonyl group of the quinone. This intermediate is then spontaneously converted to the anil structure shown below.

Compound E is the predominant product obtained, however, some of F may also be present in minor amounts. The term St indicates the remainder of the steroid ring system beginning at C$_{17}$. The substituent X is any group which will allow anil formation. This group is preferably t-butyl although other alkyls may be employed.

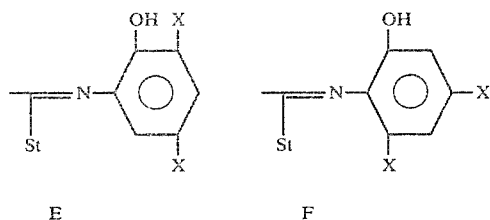

E        F

The 3,5-di-substituted quinone is added on an equivalent or 1:1 molar basis to the free amine in order to form the steroidal anil. The process is best conducted in an inert atmosphere preferably one in which nitrogen gas is used as the blanketing agent. The temperature range of the anil formation is conveniently at from about −10° C. to about 35° C.

The reaction of the steroidal amine and the 3,5-di-substituted orthoquinone to form the anil is conveniently run in an alcohol such as methanol, ethanol, isopropanol or butanol. Preferably, methanol or ethanol is employed, most preferably methanol.

The hydrolysis step is conveniently conducted at an acid pH, preferably from about 2.5 to about 4.5 and in particular the pH is desirably adjusted through the use of a buffering system employing ammonium acetate and acetic acid. In the preferred aspect of the present invention, the pH during the hydrolysis step is at from 3.0 to about 4.0. The buffering system also adds sufficient water to allow the hydrolysis to proceed at a satisfactory rate; at least equivalent quantities of water are required for the hydrolysis. Base hydrolysis may be employed but product yield and purity are not consistent.

The temperature during which the hydrolysis is conducted is conveniently at from about −10° C. to about 100° C.

A further desirable ingredient in the present invention is the presence of a nonsteroidal carbonyl compound having a ketone or aldehyde group. The purpose for adding this latter mentioned component is that it is observed that higher yields and greater purity are obtained when such material is present in the reaction mixture. The material may be added prior to the hydrolysis of step (c) or prior to solvent stripping. Both hydrolysis and solvent stripping have been found to be difficult, however, the addition of the carbonyl compound overcomes this difficulty. The carbonyl compound is conveniently employed at from about 0.01 equivalent to about 10 equivalents based on the steroid.

Convenient aldehydes and ketones which may be employed herein include cyclohexanone, cyclohexenone, methyl ethyl ketone, methyl isobutyl ketone, acetone, n-butyraldehyde, and 2-ethylhexyaldehyde. It has also been observed that materials such as levulinic and pyruvic acids and their esters are also valuable in preventing loss of the end product during solvent stripping and/or preventing degradation during hydrolysis.

The preferred di-substituted orthoquinone is 3,5-di-t-butyl-o-benzoquinone, although other similar materials should be acceptable in the system. It has been found, however, that paraquinones and higher substituted quinones such as 3,4,5,6 tetrachloro orthobenzoquinone are not satisfactory in the present invention.

The following are examples of the present invention:

EXAMPLE I

The desired end products of the present invention are prepared by reacting 0.5 grams of 20-amino-3-oxo-pregn-4-ene hydrochloride with 2.85 ml. of 0.5 M sodium methoxide and 2.2 ml. of methanol. The reaction flask is evacuated three times and put under a nitrogen atmosphere. The solution is then cooled in an ice bath and 0.32 grams (1.1 eq.) of 3,5-di-t-butyl-o-benzoquinone is added and washed into the reaction with 5.0 ml. of methanol.

The system is then again evacuated three times and again put under a nitrogen atmosphere. The mixture is then stirred using ice as a coolant for a period of approximately one hour. At the end of this time, a thin layer chromotography test shows that the desired imine has been formed with very little residual amine.

At this point, 50 ml. of a 1:1 mixture of tetrahydrofuran (THF) and methanol expressed as volume which is previously degassed with nitrogen is added under a stream of nitrogen. The system is then further evacuated three times and flushed with nitrogen. The ice bath is thereafter removed and 25 ml. of 0.1 M buffer which is ammonium acetate and acetic acid at a pH of 3.8 which is also degassed with nitrogen is added under a stream of nitrogen.

The system is then again evacuated three times and put under nitrogen pressure once again. The mixture is refluxed for approximately ½ hour. At the end of this period, thin-layer chromatography shows no residual imine, and substantial quantities of progesterone (3-20-dioxo-pregn-4-ene). The solution is then cooled to room temperature and is then diluted to 500 ml. utilizing 250 ml. of the previous described THF and methanol solution, together with 175 ml. of the buffer solution. The solution is then degassed once again with nitrogen and cooled to room temperature in an ice bath, then further degassed with nitrogen. The above process gives 94% of the theoretical yield of progesterone. The example may be further improved by utilizing each of the aforementioned carbonyl compounds at a level of 0.1 equivalent in the reaction mixture when added prior to the hydrolysis step or consequently with hydrolysis.

The conversion of 20-amino-3-oxo-pregna-1,4-diene to 3,20-dioxo-pregna-1,4-diene is accomplished with similar results.

What is claimed is:

1. A process for the conversion of a member selected from the group consisting of 20-amino-3-oxo-pregn-4-ene, and 20-amino-3-oxo-pregna-1,4-diene and mixtures thereof to 3,20-dioxo-pregn-4-ene and 3,20-dioxo-pregna-1,4-diene and mixtures thereof comprising:
 (a) obtaining the 20-amino-3-oxo-pregn-4-ene and 20-amino-3-oxo-pregna-1,4-diene in the form of the free amine;
 (b) contacting the free amine of (a) with a 3,5-disubstituted orthoquinone in a sufficient amount to form the corresponding steroidal anil; and,
 (c) hydrolyzing the steroidal anil formed in (b) to obtain the 3,20-dioxo-pregn-4-ene and 3,20-dioxo-pregna-1,4-diene and mixtures thereof.

2. The process of claim 1 wherein the steroid is initially present in the form of a salt.

3. The process of claim 2 wherein the salt is the hydrohalide.

4. The process of claim 3 wherein the hydrohalide is the hydrochloride.

5. The process of claim 2 wherein the salt is converted to the free amine through the use of a strong base.

6. The process of claim 5 wherein the strong base is a member selected from the group consisting of sodium hydroxide, potassium hydroxide, and sodium methoxide and mixtures thereof.

7. The process of claim 1 conducted in an inert atmosphere.

8. The process of claim 1 wherein step (c) is conducted at a pH at from about 2.5 to about 4.5.

9. The process of claim 8 wherein the pH is adjusted to the desired range through the use of a buffering system containing ammonium acetate and acetic acid.

10. The process of claim 9 wherein the pH is at from about 3.0 to about 4.0.

11. The process of claim 7 wherein the inert atmosphere is nitrogen.

12. The process of claim 5 wherein the strong base is sodium methoxide.

13. The process of claim 1 wherein a non-steroidal carbonyl compound is present prior to isolation of the product of step (c).

14. The process of claim 13 wherein the carbonyl compound is a ketone.

15. The process of claim 13 wherein the carbonyl compound is selected from the group consisting of methyl ethyl ketone, methyl isobutyl ketone, n-buteraldehyde, benzaldehyde, 2-ethylhexanal, levulinic acid, pyruvic acid, acetone, cyclohexanone, and cyclohexenone and mixtures thereof.

16. The process of claim 13 wherein the ketone is cyclohexanone.

17. The process of claim 1 wherein the 3,5-disubstituted orthoquinone is dialkyl substituted.

18. The process of claim 16 wherein the 3,5-disubstituted orthoquinone is 3,5-di-t-butyl orthobenzoquinone.

19. The process of claim 1 wherein component (a) is 20-amino-3-oxo-pregn-4-ene.

20. The process of claim 1 wherein component (a) is 20-amino-3-oxo-pregna-1,4-diene.

21. A member selected from the group consisting of the steroidal anil of 20-amino-3-oxo-pregn-4-ene and 20-amino-3-oxo-pregna-1,4-diene and mixtures thereof.

* * * * *